United States Patent
Chen et al.

(10) Patent No.: US 9,056,156 B2
(45) Date of Patent: Jun. 16, 2015

(54) MEDICAL DEVICES COMPRISING POLYMERIC DRUG DELIVERY SYSTEMS WITH DRUG SOLUBILITY GRADIENTS

(71) Applicant: Medtronic Vascular, Inc., Santa Rosa, CA (US)

(72) Inventors: Mingfei Chen, Santa Rosa, CA (US); Peiwen Cheng, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/473,579

(22) Filed: Aug. 29, 2014

(65) Prior Publication Data

US 2014/0370071 A1    Dec. 18, 2014

Related U.S. Application Data

(62) Division of application No. 11/780,713, filed on Jul. 20, 2007, now Pat. No. 8,852,620.

(51) Int. Cl.

| | |
|---|---|
| *A61F 2/00* | (2006.01) |
| *A61L 31/10* | (2006.01) |
| *A61L 27/34* | (2006.01) |
| *A61L 27/54* | (2006.01) |
| *A61L 29/08* | (2006.01) |
| *A61L 29/16* | (2006.01) |
| *A61L 31/16* | (2006.01) |
| *A61L 31/04* | (2006.01) |
| *C08F 220/12* | (2006.01) |
| *C08F 226/10* | (2006.01) |

(52) U.S. Cl.
CPC .................. *A61L 31/10* (2013.01); *A61L 27/34* (2013.01); *A61L 27/54* (2013.01); *A61L 29/085* (2013.01); *A61L 29/16* (2013.01); *A61L 31/16* (2013.01); *A61L 2300/416* (2013.01); *A61L 2300/60* (2013.01); *A61L 31/048* (2013.01); *A61L 2420/02* (2013.01); *C08F 220/12* (2013.01); *C08F 226/10* (2013.01)

(58) Field of Classification Search
None
See application file for complete search history.

(56) References Cited

U.S. PATENT DOCUMENTS

| | | |
|---|---|---|
| 5,362,718 A | 11/1994 | Skotnicki et al. |
| 5,858,653 A | 1/1999 | Duran et al. |
| 6,015,815 A | 1/2000 | Mollison |
| 6,214,901 B1 | 4/2001 | Chudzik et al. |
| 6,278,018 B1 | 8/2001 | Swan |
| 6,329,386 B1 | 12/2001 | Mollison |
| 7,041,308 B2 | 5/2006 | Shalaby et al. |
| 7,442,721 B2 | 10/2008 | Cheng et al. |
| 7,691,402 B2 | 4/2010 | Guo et al. |
| 7,815,927 B2 | 10/2010 | Cheng et al. |
| 2004/0106987 A1* | 6/2004 | Palasis et al. ................. 623/1.42 |
| 2005/0049271 A1 | 3/2005 | Benjamin et al. |
| 2005/0084515 A1 | 4/2005 | Upidi et al. |
| 2006/0025516 A1 | 2/2006 | Shalaby et al. |
| 2006/0099235 A1 | 5/2006 | Blakstvedt et al. |
| 2006/0230476 A1* | 10/2006 | Atanasoska et al. .......... 977/933 |
| 2006/0275340 A1 | 12/2006 | Udipi et al. |
| 2007/0122443 A1 | 5/2007 | Narayanan et al. |
| 2008/0107704 A1* | 5/2008 | Guo .............................. 424/423 |
| 2008/0233168 A1 | 9/2008 | Cheng et al. |
| 2009/0176951 A1* | 7/2009 | Matyjaszewski et al. ..... 526/200 |
| 2010/0010103 A1* | 1/2010 | Schmidt et al. ............ 514/772.1 |
| 2010/0247597 A1 | 9/2010 | Chen et al. |

FOREIGN PATENT DOCUMENTS

| | | |
|---|---|---|
| EP | 1790702 | 5/2007 |
| WO | WO 2007025086 A2 * | 3/2007 |

OTHER PUBLICATIONS

Matyjaszehski et al "Gradient copolymers by atom transfer radical copolymerization" Journal of Physical Organic Chemistry, 13; 2000, p. 775-786.*
Oh et al "Biodegradable Nanogels Prepared by Atom Transfer Radical Polymerization as Potential Drug Delivery Carriers: Synthesis, Biodegradation, in Vitro Release and Bioconjugation" JACS, published on Wed on Apr. 18, 2007, 129, p. 5939-5945.*
Matyjaszewski et al. << Controlled/Living Radical Polymerization >> Materials Today, Mar. 2005 (p. 26-33).

* cited by examiner

*Primary Examiner* — Susan Tran

(57) ABSTRACT

Disclosed are drug delivery systems comprising drugs admixed with polymers having drug solubility gradients and methods of making the polymers. Also disclosed are medical devices having coatings thereon comprising the drug solubility gradient-containing polymers and at least one drug.

12 Claims, 2 Drawing Sheets

MEDICAL DEVICES COMPRISING POLYMERIC DRUG DELIVERY SYSTEMS WITH DRUG SOLUBILITY GRADIENTS

RELATED APPLICATIONS

This application is a Division of and claims the benefit of U.S. patent application Ser. No. 11/780,713 filed Jul. 20, 2007, now allowed. The disclosures of which are herein incorporated by reference in their entirety.

FIELD OF THE INVENTION

The present invention relates to medical devices comprising drug delivery systems with drug solubility gradients for the controlled release of drugs and methods of making the drug solubility gradients.

BACKGROUND OF THE INVENTION

The implantation of medical devices has become a relatively common technique for treating a variety of medical or disease conditions within a patient's body. Depending upon the conditions being treated, today's medical implants can be positioned within specific portions of a patient's body where they can provide beneficial functions for periods of time ranging from days to years. A wide variety of medical devices can be considered implants for purposes of the present invention. Such medical devices can include structural implants such as stents and internal scaffolding for vascular use, replacement parts such as vascular grafts, or in-dwelling devices such as probes, catheters and microparticles for monitoring, measuring and modifying biological activities within a patient's cardiovascular system. Other types of medical implants for treating different types of medical or disease conditions can include in-dwelling access devices or ports, valves, plates, barriers, supports, shunts, discs, and joints, to name a few.

For example, cardiovascular disease, commonly referred to as atherosclerosis, remains a leading cause of death in developed countries. Atherosclerosis is a disease that results in the narrowing, or stenosis, of blood vessels which can lead to heart attack or stroke if the narrowing progresses to the point of blocking blood flow through the narrowed blood vessels forming the coronary arteries. Cardiovascular disease caused by stenotic or narrowed coronary arteries is commonly treated using either a coronary artery by-pass graft (CABG) around the blockage, or a procedure called angioplasty where a balloon catheter is inserted into the blocked coronary artery and advanced until the vascular stenosis is reached by the advancing balloon. The balloon is then inflated to deform the stenosis open, restoring blood flow.

However, angioplasty or balloon catheterization can result in internal vascular injury which may ultimately lead to reformation of narrowing vascular deposits within the previously opened artery. This biological process whereby a previously opened artery becomes re-occluded is referred to as restenosis. One angioplasty variation designed to reduce the possibility of restenosis includes the subsequent step of arterial stent deployment within the stenotic blockage opened by the expanded balloon. After arterial patency has been restored by expanding the angioplasty balloon to deform the stenotic lesion open, the balloon is deflated and a vascular stent is inserted into the tubular bore or vessel lumen across the stenosis site. The catheter is then removed from the coronary artery lumen and the deployed stent remains implanted across the opened stenosis to prevent the newly opened artery from constricting spontaneously or narrowing in response to the internal vascular injury resulting from the angioplasty procedure itself. However, it has been found that in some cases of angioplasty and angioplasty followed by stent deployment that restenosis may still occur.

Treating restenosis generally requires additional, more invasive, procedures including CABG in some cases. Consequently, methods for preventing restenosis, or for treating incipient forms of restenosis, are being aggressively pursued. One promising method for preventing restenosis is the administration of medicaments that block the local invasion or activation of monocytes, white blood cells that respond to injury or infection, thus preventing the associated secretion of growth factors within the blood vessel at the restenosis site that can trigger vascular smooth muscle cell (VSMC) proliferation and migration causing thickening of the vessel wall and subsequent narrowing of the artery. Metabolic inhibitors such as anti-neoplastic agents are currently being investigated as potential anti-restenotic compounds for such purposes. However, the toxicity associated with the systemic administration of known metabolic inhibitors has more recently stimulated development of in situ or site-specific drug delivery designed to place the anti-restenotic compounds directly at the target site within the potential restenotic lesion rather than generally administering much larger, potentially toxic doses to the patient.

For example, one particular site-specific drug delivery technique known in the art employs the use of vascular stents coated with anti-restenotic drugs. These stents have been particularly useful because they not only provide the mechanical structure to maintain the patency or openness of the damaged vessel, but they also release the anti-restenotic agents directly into the surrounding tissue. This site specific delivery allows clinically effective drug concentrations to be achieved locally at the stenotic site without subjecting the patient to the side effects that may be associated with systemic drug delivery of such pharmaceutical compounds. Moreover, localized or site specific delivery of anti-restenotic drugs eliminates the need for more complex specific cell targeting technologies intended to accomplish similar purposes.

An important factor in the efficacy of in situ drug delivery is how the drug is attached to the stent and delivered to the target site as a result. More specifically, a sufficient amount of deliverable drug needs to be releasably attached to and associated with the stent or implantable drug delivery vehicle. Typically, as known in the art, anti-restenotic drugs are releasably attached to the surfaces of implantable drug delivery devices such as stents through chemical bonding with the surface through either non-covalent or covalent bonding. Non-covalent bonds are generally weaker than covalent chemical bonds and therefore release the bound drugs more easily. Conversely, covalent chemical bonds are generally stronger and hold on to the bound drugs more securely, providing easier handling and storage.

An alternative approach to binding pharmaceutical compounds to the surfaces of implantable medical devices utilizes coatings rather than binding the drugs directly to the surfaces of the implants. For example, drugs can be incorporated into or applied to a polymer layer that is itself applied to the surface of the implant. A variety of polymers have been developed in the art which are intended to allow for drug attachment to medical implants and for subsequent delivery. Such materials are disclosed in U.S. Pat. Nos. 6,278,018, 6,214,901, and 5,858,653, incorporated herein by reference.

As noted above, an important factor in the efficacy and the utility of such in situ drug delivery techniques and devices is the ability to release an effective dose of the drug at the appropriate time for the appropriate duration. In most prior art technologies the drug delivering implants are coated with a polymer that binds or holds the drug within the polymer coating and releases the drug as the polymer coating is broken down by normal processes within the patient's body or the drug simply diffuses out of the polymer coating once it is in an aqueous or wet environment. Typically, these drug release mechanisms result in what is known as dumping or the relatively sudden release of the majority of the bound drugs over a relatively short period of time.

Additionally, this sudden release profile results in the amount of drug being delivered to the target site rapidly tapering off over time. As a result, an effective drug dose is delivered only for a short period of time following implantation. This can result in a less than effective administration of the drug. Thus, while these prior art drug releasing coating technologies have been useful and promising, a strong need exists for a site specific drug delivery technology utilizing medical implants where the drug release profiles and the associated drug dosages can be controlled over time. It is an object of the present invention to address this and other needs.

SUMMARY OF THE INVENTION

The present invention disclosed herein provides for implantable medical devices having a gradient polymer coating wherein the polymer coating has a drug solubility gradient comprised of gradient polymers that allow for the controlled release of drugs.

In one embodiment of the present invention, a medical device is provided comprising a controlled-release drug delivery system comprising a drug admixed with a polymer, the aforementioned polymer comprising a drug solubility gradient. In one embodiment of the invention, the admixed drug is hydrophobic. In another embodiment of the invention, the admixed drug is hydrophilic. In yet another embodiment, a medical device is provided wherein the polymeric drug solubility gradient comprises at least two monomers selected from the group comprising ε-caprolactone, polyethylene glycol (PEG), trimethylene carbonate, lactide, glycolide, p-dioxanone, methyl methacrylate, ethy methacrylate, propyl methacryalte, butyl methacrylate, pentyl methacrylate, hexyl methacrylate, heptyl methacrylate, octyl methacryalte, dodecylmethacryalte, 2-(ethoxy ethyl methacrylate), glycidyl methacrylate, poly(ethylene glycol) methacrylate, methyl acrylate, ethy acrylate, propyl acryalte, butyl acrylate, pentyl acrylate, hexyl acrylate, heptyl acrylate, octyl acryalte, dodecyl acryalte, 2-ethoxyethyl acrylate, glycidyl acrylate, poly(ethylene glycol) acrylate, N-vinyl pyrrolidinone, and derivatives thereof. In yet another embodiment a medical device is provided wherein the monomers comprise hexyl methacrylate and N-vinyl pyrrolidinone.

In another embodiment of the present invention, a medical device is provided wherein the drug is selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

In another embodiment of the present invention a medical device is provided wherein the drug comprises at least one compound selected from the group consisting of sirolimus (rapamycin), tacrolimus (FK506), everolimus (certican), temsirolimus (CCI-779) and zotarolimus (ABT-578). In another embodiment of the invention, the drug comprises zotarolimus. In yet another embodiment of the present invention, the medical device comprises more than one drug.

In another embodiment of the current invention, the drug solubility gradient comprises regions of greater relative hydrophobicity and regions of greater relative hydrophilicity. In another embodiment of the invention, the regions of greater hydrophobicity and regions of greater relative hydrophilicity comprise a continuous gradient. In yet another embodiment of the invention, the regions of greater hydrophobicity and regions of greater relative hydrophilicity comprise a discontinuous gradient.

In another embodiment of the current invention, the medical device is selected from the group consisting of vascular stents, stent grafts, urethral stents, bile duct stents, catheters, guide wires, pacemaker leads, bone screws, sutures, and prosthetic heart valves. In yet another embodiment of the current invention, the medical device is a vascular stent.

In another embodiment of the current invention, the medical device is a vascular stent comprising a controlled-release drug delivery system comprising a drug admixed with a polymer comprising a drug solubility gradient, the polymer comprising hexyl methacrylate and N-vinyl-pyrrolidinone.

Another embodiment of the current invention comprises a method of preparing a drug solubility gradient. The method comprises preparing a first charge solution further comprising at least one monomer under conditions that promote polymerization. The method further comprises preparing at least one additional charge solution comprising at least one monomer. The additional charge solution is added to the first charge solution and reacted. The first charge solution and the additional charge solution are reacted until the desired degree of polymerization has been reached. In the present invention, the additional charge solution comprises from 2 to 10 charge solutions.

In another embodiment of the current invention, the adding step comprises a continuous addition of the additional charge solution to the first charge solution. In yet another embodiment of the invention, the adding step comprises a discontinuous addition of the additional charge solution to the first solution.

In another embodiment of the current invention, the method comprises preparing a third solution comprising at least one monomer and adding the third solution to the mixture of the first solution and the additional charge solution. The first solution, additional charge solution, and the third solution are reacted until the desired degree of polymerization has been reached.

In another embodiment of the current invention, the monomer is selected from the group comprising ε-caprolactone, polyethylene glycol (PEG), trimethylene carbonate, lactide, glycolide, p-dioxanone, methyl methacrylate, ethy methacrylate, propyl methacryalte, butyl methacrylate, pentyl methacrylate, hexyl methacrylate, heptyl methacrylate, octyl methacryalte, dodecylmethacryalte, 2-(ethoxy ethylmethacrylate), glycidyl methacrylate, poly(ethylene glycol) methacrylate, methyl acrylate, ethy acrylate, propyl acryalte, butyl acrylate, pentyl acrylate, hexyl acrylate, heptyl acrylate, octyl acryalte, dodecyl acryalte, 2-ethoxyethyl acrylate, glycidyl acrylate, poly(ethylene glycol) acrylate, N-vinyl pyrrolidinone, and derivatives thereof.

In yet another embodiment of the current invention, the drug solubility gradient further contains at least one drug. In another embodiment, the drug is selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. In another embodiment of the invention, the drug comprises at least one compound selected from the group consisting of sirolimus (rapamycin), tacrolimus (FK506), everolimus (certican), temsirolimus (CCI-779) and zotarolimus (ABT-578).

In yet another embodiment of the current invention, the method comprises the step of coating the polymer comprising a drug solubility gradient on a vascular stent. In yet another embodiment, the method comprises the step of fabricating a vascular stent from the polymer comprising a drug solubility gradient.

DEFINITION OF TERMS

Figure 1:
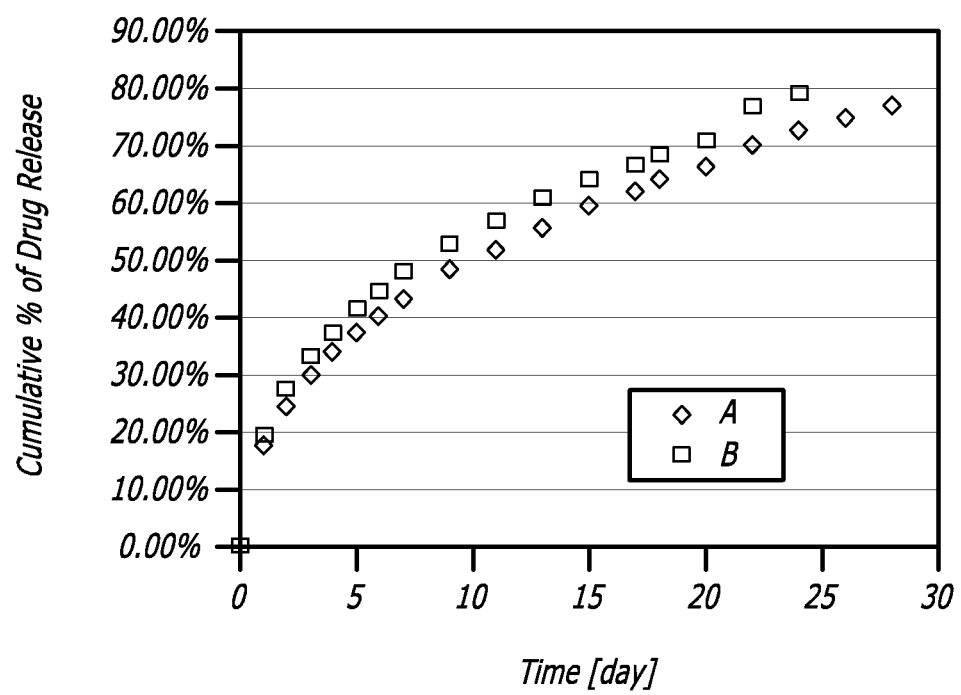
FIG. 1 depicts release of ABT-578 from vascular stents coated with gradient polymers made according to the teachings of the present invention.

Amphiphilic: As used herein, "amphiphilic" refers to a polymer or polymer region having a relatively equivalent affinity for both hydrophilic and hydrophobic drugs.

Backbone: As used herein, "backbone" refers to the main chain of a polymer or copolymer of the present invention. A "polyester backbone" as used herein refers to the main chain of a biodegradable polymer comprising ester linkages. A "polyether backbone" as used herein refers to the main chain of a biodegradable polymer comprising ether linkages. An exemplary polyether is polyethylene glycol (PEG).

Biocompatible: As used herein, "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Copolymer: As used herein, a "copolymer" is a macromolecule produced by the simultaneous or step-wise polymerization of two or more dissimilar units such as monomers. Copolymers include bipolymers (two dissimilar units), terpolymers (three dissimilar units), etc.

Controlled release: As used herein, "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Drug(s): As used herein, "drug" shall include any bioactive agent or pharmaceutical compound having a therapeutic effect in an animal. Exemplary, non limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP 12 binding compounds include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid) and zotarolimus (ABT-578). Additionally, and other rapamycin hydroxyesters may be used in combination with the drug delivery systems of the present invention.

Drug Solubility Gradient: As used herein, "drug solubility gradient" refers to polymers having varying ratios of monomers throughout the material resulting in polymers having a directional gradient or alternatively non-uniform distribution, of hydrophobic and/or hydrophilic monomers throughout.

Ductility: As used herein, "ductility", or "ductile" is a polymer attribute characterized by the polymer's resistance to fracture or cracking when folded, stressed or strained at operating temperatures. When used in reference to the polymer coating compositions of the present invention the normal operating temperature for the coating will be between room temperature and body temperature or approximately between 15° C. and 40° C. Polymer durability in a defined environment is often a function of its elasticity/ductility.

Glass Transition Temperature ($T_g$): As used herein, "glass transition temperature" ($T_g$) refers to a temperature wherein a polymer structurally transitions from a elastic pliable state to a rigid and brittle state.

Hydrophilic Drug: As used herein in reference to the drug, the term "hydrophilic" refers to a bioactive agent that has solubility in water of more than 200 micrograms per milliliter.

Hydrophilic: As used herein in reference to a polymer, the term "hydrophilic" refers to a polymer or polymer region that contains greater than 50% hydrophilic monomers and has affinity for hydrophilic drugs.

Hydrophobic Drug: As used herein in reference to the drug, the term "hydrophobic" refers to a bioactive agent that has solubility in water of no more than 200 micrograms per milliliter.

Hydrophobic: As used herein in reference to a polymer, the term "hydrophobic" refers to a polymer or polymer region that contains greater than 50% hydrophobic monomers and has affinity for hydrophobic drugs.

$M_n$: As used herein, $M_n$ refers to number-average molecular weight. Mathematically it is represented by the following formula:

$$M_n = \Sigma_i N_i M_i / \Sigma_i N_i,$$

wherein the $N_i$ is the number of moles whose weight is $M_i$.

$M_w$: As used herein, $M_w$ refers to weight average molecular weight that is the average weight that a given polymer may have. Mathematically it is represented by the following formula:

$$M_w = \Sigma_i N_i M_i^2 / \Sigma_i N_i M_i,$$

wherein $N_i$ is the number of molecules whose weight is $M_i$.

DETAILED DESCRIPTION OF THE INVENTION

The present invention provides drug-delivery systems comprising drug solubility gradients for the controlled release of drugs and methods for making the gradients. The release profile of one or more drugs reversibly associated with the polymers comprising drug solubility gradients is controlled to provide time released targeted in situ drug delivery of effective amounts of the bioactive agents. Moreover, the gradient polymers of the present invention can be tuned, modified, to vary the rates of drug elution as well as allow for various drugs to be eluted.

The drug solubility gradients in the polymers are formed by varying the monomer feeding (addition of monomers during the polymerization process) concentration and composition over time during the synthesis of the polymers. Forming the drug solubility gradients includes changing temperatures, pressures, and monomer ratios and selection during synthesis.

The polymers having drug solubility gradients are formed from two or more polymerizable monomers including, but not limited to, ε-caprolactone, polyethylene glycol (PEG), trimethylene carbonate, lactide, glycolide, p-dioxanone, methyl methacrylate, ethyl methacrylate, propyl methacrylalte, butyl methacrylate, pentyl methacrylate, hexyl methacrylate, heptyl methacrylate, octyl methacryalte, dodecylmethacryalte, 2-(ethoxy ethyl methacrylate), glycidyl methacrylate, poly(ethylene glycol) methacrylate, methyl acrylate, ethy acrylate, propyl acryalte, butyl acrylate, pentyl acrylate, hexyl acrylate, heptyl acrylate, octyl acrylate, dodecyl acrylate, poly(ethylene glycol) acrylate, N-vinyl pyrrolidinone and derivatives thereof.

The drug solubility gradient within the polymer, without being bound to the theory, supports effective drug eluting profiles by providing a locally hospitable environment for both the physiological medium and the drug to be eluted. Monomers compatible with hydrophilic drugs can increase the physical attraction of hydrophilic drugs to the polymer while monomers compatible with hydrophobic drugs can increase the physical attraction of hydrophobic drugs to the polymer. The hydrophobicity, hydrophilicity and/or amphiphilicity of regions of the polymers can be tuned by increasing or decreasing the concentration and composition of the appropriate monomers during synthesis.

Figure 2:
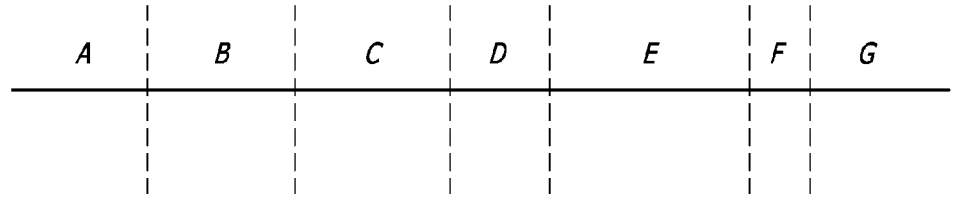
FIG. 2 graphically depicts an exemplary drug solubility gradient according to the teachings of the present invention.
Figure 4:
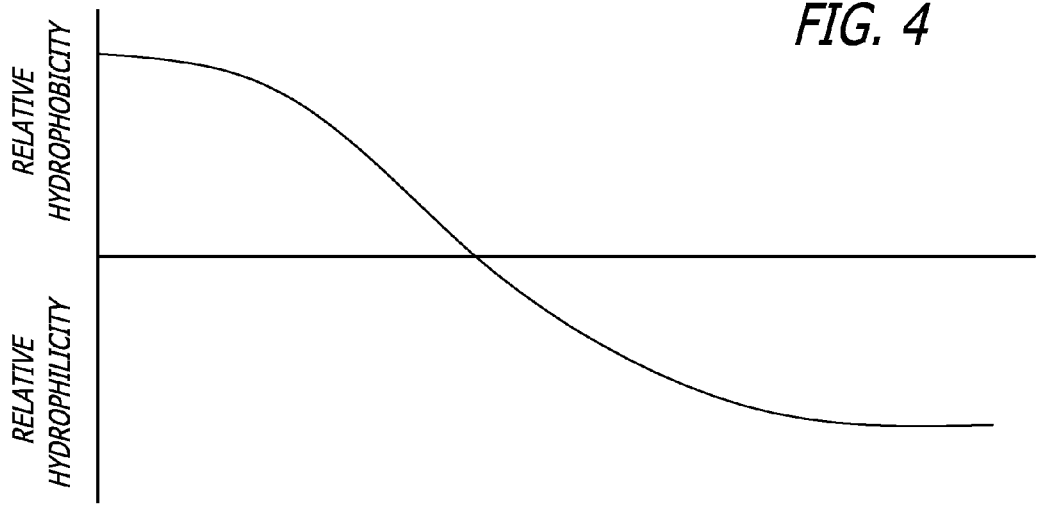
FIG. 4 graphically depicts one embodiment of a drug solubility gradient according to the teachings of the present invention.

FIG. 2 depicts one embodiment of the drug solubility gradient of the present invention. FIG. 2 depicts a polymer having a drug solubility gradient comprising regions A through G, each representing different relative hydrophobicities. For example, and not intended as a limitation, the gradient polymer of FIG. 2 can be continuous wherein region A is an area of high relative hydrophobicity and each subsequent region, A through F, represents an area of lower relative hydrophobicity and region G represents the area of lowest relative hydrophobicity in the polymer. FIG. 4 depicts one embodiment of the present invention wherein the drug solubility gradient is continuous from high relative hydrophobicity composition to high relative hydrophilicity composition (low relative hydrophobicity). Conversely, in another non-limiting example, region A has the lowest relative hydrophobicity and region G has the highest relative hydrophobicity. During the transition from high hydrophobicity to low hydrophobicity there may exist regions of amphiphilicity.

Figure 3:
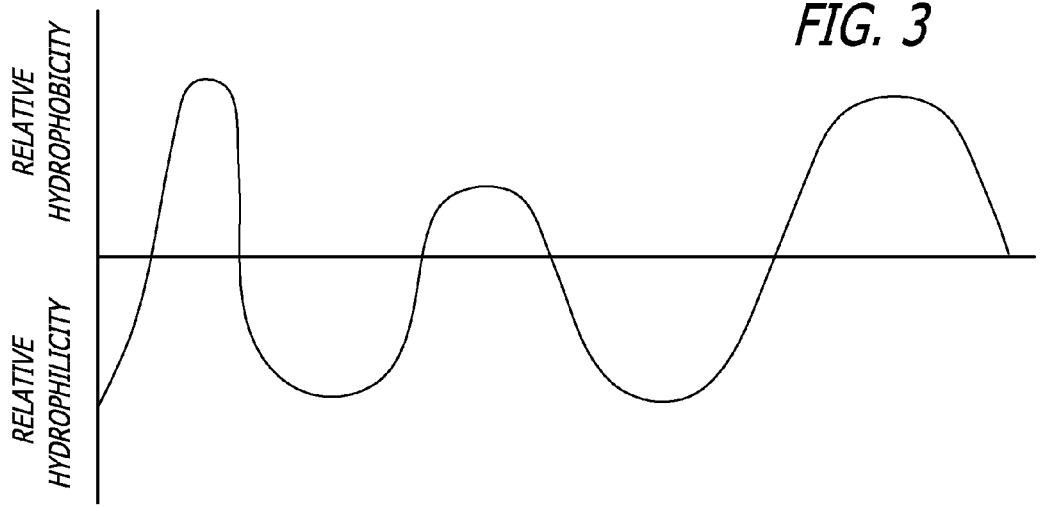
FIG. 3 graphically depicts one embodiment of a drug solubility gradient according to the teachings of the present invention.

Additionally, the drug solubility gradients of the present invention can be discontinuous. Again referring to FIG. 2, in the discontinuous drug solubility gradient of the present invention, each of regions A through G comprises a different relative hydrophobicity. For example, and not intended as a limitation, and illustrated in FIG. 3, region A has high relative hydrophobicity, region B is amphiphilic, region C is high relative hydrophilicity, region D has high relative hydrophobicity, etc. The number of regions in the discontinuous drug solubility gradient is not limited to the regions depicted in either of FIG. 2 or 3 and can be any number of regions only limited by the number of steps in the synthetic process.

In general, the polymers of the present invention are synthesized by the following method. Selected monomers are allowed to polymerize contemporaneous with the injection of an additional solution containing one or more additional monomers into the reaction mixture at a predetermined rate. The injection of monomers into the reaction mixture allows for the gradient to be established.

More specifically, a solution of at least one monomer, charge solution 1, is allowed to polymerize while another solution of at least one monomer, charge solution 2, is injected into charge solution 1 at predetermined rate. The polymers of the present invention are synthesized with at least two charge solutions, each charge solution comprising at least one polymerizable monomer. In one embodiment, the polymers are synthesized with three charge solutions. In another embodiment of the present invention, the polymers are synthesized with four charge solutions. In yet another embodiment, the polymer is synthesized with up to 100 charge solutions. Each charge solution comprises at least one monomer and is comprised of monomers that are either the same or different than other charge solutions for synthesizing a particular polymer.

In one embodiment of the present invention, the second and subsequent charge solutions are added to the first charge solution sequentially. In another embodiment, the second and subsequent charge solutions are added in any order at any time and in any combination after the initiation of the reaction in the first charge solution.

In another embodiment of the present invention, second and subsequent charge solutions are added to the first charge solution at a constant rate or a discontinuous rate.

In a non-limiting example, the drug solubility gradient in the polymer is established by a continuous change in monomer concentration or composition over the synthetic growth of the polymer. For example, a non-limiting gradient is established by starting with charge solution 1 comprising a 50:50 ratio of monomer A and monomer B, and injecting charge solution 2 comprising a 75:25 ratio of monomer A and monomer B into the reaction mixture at a predetermined rate.

In another embodiment, the additional gradient is established by adding additional different monomers during the synthetic process. In a non-limiting example, a gradient is formed by starting with charge 1 solution comprising a 50:50 ratio of monomer A: monomer B, and charge 2 solution comprising a 50:25:25 ratio of monomer A: monomer B: monomer C is added to the reaction mixture, thus creating the gradient in the final polymer.

In another exemplary embodiment, the additional gradient is established by starting with a charge solution 1 comprising a 50:50 ration of monomer A: monomer B and adding charge solution 2 comprising a single monomer including monomer A, monomer B or a third monomer type. Further charge solutions containing the same or different monomers in the same or different ratios are optionally added to the reaction mixture.

The polymers having drug solubility gradient according to the present invention form controlled-release drug delivery systems when admixed with therapeutic drugs rendering the systems useful for the delivery and controlled release of drugs to local sites. In one embodiment, at least one drug is incorporated into the drug delivery system. Drugs that are suitable for release from the drug solubility gradient-containing polymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention the drugs controllably released from the polymers include, but are not limited to, macrolide antibiotics including FKBP-12 binding agents. Exemplary drugs of this class include sirolimus (rapamycin) (Formula 2), tacrolimus (FK506), everolimus (certican or RAD-001), temsirolimus (CCI-779) and zotarolimus (ABT-578; see U.S. Pat. Nos. 6,015,815 and 6,329,386) (Formula 1). Additionally, amorphous rapamycin 42-ester with 3-hydroxy-2-(hydroxymethyl)-2-methylpropionic acid as disclosed in U.S. patent application Ser. No. 10/930,487 and other rapamycin hydroxyesters (including temsirolimus) as disclosed in U.S. Pat. No. 5,362,718 may be used in combination with the polymers of the present invention. The entire contents of all of preceding patents and patent applications are herein incorporated by reference for all they teach related to FKBP-12 binding compounds and the derivatives.

Formula 1

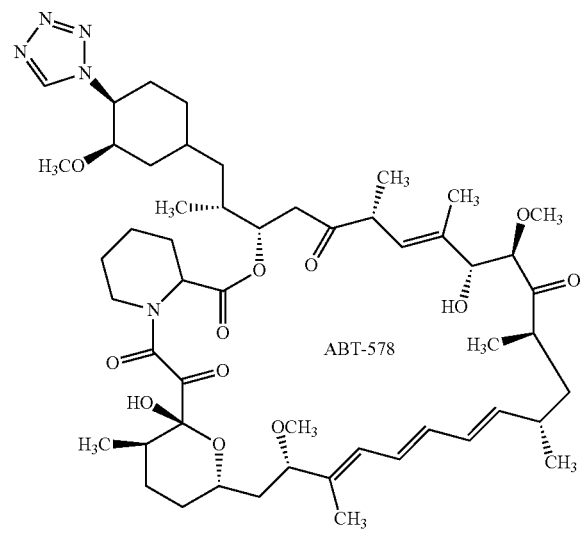

Formula 2

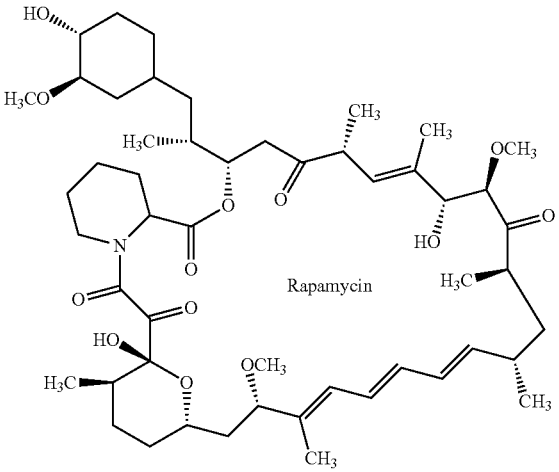

The drug delivery systems of the present inventions are particularly useful for coating implantable medical devices including, but not limited to, vascular stents, stent grafts, urethral stents, bile duct stents, catheters, guide wires, pacemaker leads, bone screws, sutures and prosthetic heart valves. Furthermore, the polymers of the present invention are suitable for fabricating medical devices including, but are not limited to, vascular stents, stent grafts, urethral stents, bile duct stents, catheters, guide wires, pacemaker leads, bone screws, sutures and prosthetic heart valves. In one embodiment of the present invention the drug delivery systems of the present invention are used to coat vascular stents.

The present invention also provides drug solubility gradient-containing polymers with variable properties that include glass transition temperatures ($T_g$). Physical properties of the polymers can be fine tuned so that they can optimally perform for their intended use. Properties that can be fine tuned, without limitation, include $T_g$, molecular weight (both $M_n$ and $M_w$), polydispersity index (PDI, the quotient of $M_w/M_n$), and degree of elasticity and degree of amphiphlicity.

In one embodiment of the present invention, the $T_g$ of the drug solubility gradient-containing polymers range from about $-10°$ C. to about $85°$ C. In another embodiment, the $T_g$ ranges from about $0°$ C. to about $40°$ C. In another embodiment, the $T_g$ ranges from about $10°$ C. to about $35°$ C. In another embodiment, the $T_g$ ranges from about $15°$ C. to about $30°$ C. In another embodiment, the $T_g$ ranges from about $20°$ C. to about $25°$ C. In still another embodiment of the present invention, the PDI of the drug solubility gradient-containing polymers range from about 1.3 to about 4.0. In still another embodiment, the PDI ranges from about 1.5 to about 3.5. In still another embodiment, the PDI ranges from about 2.0 to about 3.0. In still another embodiment, the PDI ranges from about 2.5 to about 2.7.

Drug elution from polymers depends on many factors including polymer density. The drug to be eluted, molecular nature of the polymer and $T_g$, among other properties. Higher $T_g$s, for example temperatures above $40°$ C., result in more brittle polymers while lower $T_g$s, e.g. lower than $40°$ C., result in more pliable and elastic polymers. In the present invention $T_g$ can be controlled, such that the polymer elasticity and pliability can be varied as a function of temperature. The mechanical properties dictate the use of the polymers, for example, drug elution is slow from polymers that have high $T_g$s while faster rates of drug elution are observed with polymers possessing low $T_g$s.

Coating polymers having relatively high $T_g$s can result in medical devices with unsuitable drug eluting properties as well as unwanted brittleness. In the cases of polymer-coated vascular stents, a relatively low $T_g$ in the coating polymer effects the deployment of the vascular stent. For example, polymer coatings with low $T_g$s are "sticky" and adhere to the balloon used to expand the vascular stent during deployment, causing problems with the deployment of the stent. Low $T_g$ polymers, however, have beneficial features in that they are more elastic at a given temperature than polymers having higher $T_g$s. Expanding and contracting a polymer-coated vascular stent mechanically stresses the coating. If the coating is too brittle, i.e. has a relatively high $T_g$, then fractures may result in the coating possibly rendering the coating inoperable. If the coating is elastic, i.e. has a relatively low $T_g$, then the stresses experienced by the coating are less likely to mechanically alter the structural integrity of the coating. Therefore, the $T_g$s of the drug solubility gradient-containing polymers of the present invention can be fine tuned for appropriate coating applications by a combination of monomer composition and synthesis conditions. The drug solubility gradient-containing polymers of the present invention are engineered to have adjustable physical properties enabling the practitioner to choose the appropriate polymer for the chosen function.

In order to tune, or modify, the drug solubility gradient-containing polymers of the present invention, a variety of properties are considered including, but not limited to, $T_g$, connectivity, molecular weight and thermal properties.

In the present invention, the balance between the hydrophobic and hydrophilic properties in the drug solubility gradient-containing polymer is controlled and can be tailored to a wide range of drugs. For example, increasing the hydrophobic nature of the gradient polymer increases the gradient polymer's compatibility with hydrophobic drugs. Additionally, the gradient polymers can be tailored to adhere to the particular medical device.

The methods described are also useful for coating only a portion of the implantable medical device such that the medical device contains portions that provide the beneficial effects of the coating and portions that are uncoated. The coating steps can be repeated or the methods combined to provide a plurality of layers of the same coating or a different coating. In one embodiment, each layer of coating comprises a different polymer or the same polymer. In another embodiment each layer comprises the same drug or a different drug. Furthermore, the drug solubility gradient-containing polymer-coated medical device can further comprise a top, or cap, coat. A cap coat as used here refers to the outermost coating layer applied over another coating. A drug-releasing drug solubility gradient-containing polymer coating is optionally applied over the primer coat. A polymer cap coat is applied over the drug-releasing gradient polymer coating. The cap coat may optionally serve as a diffusion barrier to further control the drug release, or provide a separate drug. The cap coat may be merely a biocompatible polymer applied to the surface of the sent to protect the stent and have no effect on elution rates.

Depending upon the type of materials used to form the drug solubility gradient-containing polymer coatings of the present invention, the coatings can be applied to the surface of a medical device, either primed or bare, through any of the coating processes known or developed in the art. Application methods compatible with the present invention include, but are not limited to, spraying, dipping, brushing, vacuum-deposition, and others. One method includes directly bonding the gradient polymer to the implant's surface. By directly attaching the polymer coating to the device, covalent chemical bonding techniques are utilized. Generally, the device surface possesses chemical functional groups on its surface such as carbonyl groups, primary amines, hydroxyl groups, or silane groups which will form strong, chemical bonds with similar groups on the active compounds utilized. In the absence of such chemical forming functional group, known techniques can be utilized to activate the material's surface before coupling the biological compound. Surface activation is a process of generating, or producing, reactive chemical functional groups using chemical or physical techniques such as, but not limited to, ionization, heating, photochemical activation, oxidizing acids, and etching with strong organic solvents.

Alternatively, the gradient polymer coating can be indirectly bound to the device's surface through an intermediate layer. This intermediate layer can be either covalently bound to the fixed substrate's surface or bonded through intermolecular attractions such as ionic or Van der Waals forces. Examples of commonly used intermediate layers within the scope of the present invention include, but are not limited to, organic polymers such as silicones, polyamines, polystyrene, polyurethane, acrylates, methoxysilanes, and others.

According to the teachings of the present invention, the medical device also can be provided with a non-erodable base coating. The base coating can be provided so as to enhance the biocompatibility of the device. Exemplary base coatings can be selected from the group consisting of polyurethanes, silicones and polysilanes. Other polymers that can be utilized include polyolefins, polyisobutylene and ethylene-alphaolefin copolymers; acrylic polymers and copolymers, ethylene-co-vinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; and carboxymethyl cellulose. In accordance with the teachings of the present invention, the base coating can also include, without limitation, antibiotics, anti-inflammatory agents, lubricity-enhancing agents, anti-coagulants, anti-metabolites, anti-thrombogenic agents, immunosuppressive agents, muscle relaxants, proteins, peptides, and hormones.

EXAMPLES

The following non limiting examples provide methods for the synthesis of exemplary polymers according to the teachings of the present invention.

Example 1

Example 1 illustrates the synthesis of copolymer A having a gradient comprising hexyl methacrylate and N-vinyl pyrrolidinone.

Charge number 1 solution was prepared in the following manner: A bottle with a magnetic spin bar was charged with 0.6 g of N-vinyl pyrrolidinone, 2.4 g of hexyl methacraylate, 13 g of 2-butenone and 75 mg of azobisisobutyronitrile. The bottle was sealed, stirred, and purged with nitrogen for 20 minutes.

Charge number 2 solution was prepared in the following manner: A bottle with a magnetic spin bar was charged with 7.2 g of N-vinyl pyrrolidinone, 7.2 g of hexyl methacrylate, 14.4 g of 2-butenone and 108 mg of azobisisobutyronitrile. The bottle was sealed, stirred, and purged with nitrogen for 20 minutes.

Charge number 1 bottle was heated (60° C.) in a water bath while charge number 2 solution was pumped (4 mL/h) into charge number 1 solution via a syringe pump over a period of 6 hours (total injected 24 mL). The polymer solution was poured into a cooled solution (−60° C.) of hexanes (400 mL) and the polymer was precipitated. The precipitated polymer was dissolved in warm hexanes (50° C.) and the solution cooled (−60° C.) to precipitate the polymers once more. The precipitated polymer was dissolved in chloroform and sprayed onto a Teflon tray where the polymer was dried under vacuum at 45° C.

Characterization Data: $M_w$=70,000; PDI=1.62; on average 78% hexyl methacrylate and 22% N-vinyl pyrrolidinone.

Example 2

Example 2 illustrates the synthesis of copolymer B having a gradient comprising hexyl methacrylate and N-vinyl pyrrolidinone.

Charge number 1 solution was prepared in the following manner: A bottle with a magnetic spin bar was charged with 2.47 g of N-vinyl pyrrolidinone, 0.63 g of hexyl methacrylate, 3.14 g of 1,4 dioxane and 23 mg of azobisisobutyronitrile. The bottle was sealed, stirred, and purged with nitrogen for 20 minutes.

Charge number 2 solution was prepared in the following manner: A bottle with a magnetic spin bar was charged with 3.62 g of N-vinyl pyrrolidinone, 10.97 g of hexyl methacrylate, 14.56 g of 1,4 dioxane and 108 mg of azobisisobutyronitrile. The bottle was sealed, stirred, and purged with nitrogen for 20 minutes.

Charge number 1 bottle was heated (60° C.) in a water bath while charge number 2 solution was pumped (4 mL/h) into charge number 1 solution via a syringe pump over a period of 6 hours (total injected 24 mL). The polymer solution was poured into a cooled solution (−60° C.) of hexanes (400 mL) and the polymer was precipitated. The precipitated polymer was dissolved in warm hexanes (50° C.) and the solution cooled (−60° C.) to precipitate the polymers once more. The precipitated polymer was dissolved in chloroform and sprayed onto a Teflon tray where the polymer was dried under vacuum at 45° C.

Characterization Data: $M_w$=219,000; PDI=1.86; on average 72% hexyl methacrylate and 28% N-vinyl pyrrolidinone.

Example 3

Example 3 illustrates the coating of a vascular stent with the controlled release gradient composition polymers of the present invention.

A 1% solution of a gradient polymer (such as from Examples 1 and 2) and ABT-578 (a polymer:drug ratio of 70:30 by weight) in chloroform was sprayed on a vascular stent and allowed to dry producing a controlled release coating on the vascular stent. The vascular stents were then exposed to a solvent for up to 30 days and drug release from the stent into the solvent was measured by high performance liquid chromatography (HPLC). Release of ABT-578 was well controlled from each of two different gradient polymers (the gradient polymers A and B synthesized in Examples 1 and 2) as depicted in FIG. 1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on the disclosed embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of preparing a drug solubility gradient comprising a drug admixed with a polymer, the method comprising:
   preparing a first monomeric charge solution comprising at least one monomer under conditions that promote polymerization;
   preparing at least one additional monomeric charge solution comprising at least one monomer;
   contemporaneously initiating polymerization of the at least one monomer of the first monomeric charge solution while adding said additional monomeric charge solution to said first charge monomeric solution; and
   reacting said first monomeric charge solution and said additional monomeric charge solution until the desired degree of polymerization of the polymer has been reached.

2. The method of claim 1 wherein said additional charge solution comprises from 2 to 10 charge solutions.

3. The method according to claim 1 wherein said adding step comprises a continuous addition of said additional charge solution to said first charge solution.

4. The method according to claim 1 wherein said adding step comprises a discontinuous addition of second said additional charge solution to said first solution.

5. The method according to claim 1 further comprising:
   preparing a third monomeric charge solution comprising at least one monomer;
   adding said third monomeric charge solution to the mixture of said first monomeric charge solution and said additional monomeric charge solution; and
   reacting said first monomeric charge solution and second said monomeric charge solution until the desired degree of polymerization has been reached.

6. The method according to either of claim 1 or 5 wherein said monomer is selected from the group comprising epsilon-caprolactone, polyethylene glycol (PEG), trimethylene carbonate, lactide, glycolide, p-dioxanone, methyl methacrylate, ethy methacrylate, propyl methacryalte, butyl methacrylate, pentyl methacrylate, hexyl methacrylate, heptyl methacrylate, octyl methacryalte, dodecylmethacryalte, 2-(ethoxy ethylmethacrylate), glycidyl methacrylate, poly(ethylene glycol) methacrylate, methyl acrylate, ethy acrylate, propyl acrylate, butyl acrylate, pentyl acrylate, hexyl acrylate, heptyl acrylate, octyl acryalte, dodecyl acryalte, 2-ethoxyethyl acrylate, glycidyl acrylate, poly(ethylene glycol) acrylate, N-vinyl pyrrolidinone, and derivatives thereof.

7. The method according to claim 1 wherein said drug is selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

8. The method according to claim 7 wherein said drug comprises at least one compound selected from the group consisting of sirolimus (rapamycin), tacrolimus (FK506), everolimus (certican), temsirolimus (CCI-779) and zotarolimus (ABT-578).

9. The method according to claim 1 further comprising the step of coating said polymer comprising a drug solubility gradient on a vascular stent.

10. The method according to claim 1 further comprising the step of fabricating a vascular stent from said polymer comprising a drug solubility gradient.

11. A method of preparing a drug solubility gradient comprising a drug admixed with a polymer, the method comprising:
   preparing a first monomeric charge solution comprising at least one monomer under conditions that promote polymerization;
   preparing at least one additional monomeric charge solution comprising at least one monomer;
   contemporaneously initiating polymerization of the at least one monomer of the first monomeric charge solution while adding said additional monomeric charge solution to said first charge solution; and
   reacting said first monomeric charge solution and said additional monomeric charge solution until the desired degree of polymerization of the polymer has been reached;
   wherein the polymer comprises monomers arranged in a directional gradient of different hydrophobic and/or hydrophilic monomers throughout the polymer.

12. The method according to claim 11 wherein the directional gradient forms a drug solubility gradient that is continuous throughout the polymer from a region of high relative hydrophobicity to a region of high relative hydrophilicity.

* * * * *